US008452356B2

(12) United States Patent
Vestel et al.

(10) Patent No.: US 8,452,356 B2
(45) Date of Patent: May 28, 2013

(54) OPTICAL MICRONEEDLE-BASED SPECTROMETER

(75) Inventors: Michael J. Vestel, Menlo Park, CA (US); Karen M. Nashold, Menlo Park, CA (US); Joseph R. Stetter, Menlo Park, CA (US); Diane P. Walter, Menlo Park, CA (US); Gregory W. Faris, Menlo Park, CA (US); Christopher Holland, Menlo Park, CA (US); Roger Schmidt, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 963 days.

(21) Appl. No.: 12/434,640

(22) Filed: May 2, 2009

(65) Prior Publication Data
US 2010/0121163 A1 May 13, 2010

Related U.S. Application Data

(60) Provisional application No. 61/050,157, filed on May 2, 2008.

(51) Int. Cl.
*A61B 5/00* (2006.01)

(52) U.S. Cl.
USPC .......................................................... 600/310

(58) Field of Classification Search
USPC ................. 600/310, 316, 581; 604/503, 6.04, 604/6.09; 216/2, 11, 41, 56, 67, 79; 264/154, 264/322, 328.1, 504; 436/57; 356/450
See application file for complete search history.

(56) References Cited

U.S. PATENT DOCUMENTS

| 6,049,727 | A | 4/2000 | Crothall |
| 6,122,536 | A | 9/2000 | Sun et al. |
| 2002/0020688 | A1 * | 2/2002 | Sherman et al. ................... 216/2 |
| 2006/0246592 | A1 * | 11/2006 | Hashmonay .................... 436/57 |
| 2008/0186500 | A1 * | 8/2008 | Schmidt et al. ................ 356/450 |
| 2008/0221408 | A1 * | 9/2008 | Hoarau et al. ................. 600/310 |
| 2011/0009720 | A1 * | 1/2011 | Kunjan et al. ................. 600/316 |

OTHER PUBLICATIONS

Wen et al., Optics Letters 33, 1875-77 (Aug. 15, 2008), all.
Lilienfeld-Toal et al., Vibrational Spectroscopy 38, 209-215 (May 23, 2005), all.

\* cited by examiner

*Primary Examiner* — Brian Szmal
(74) *Attorney, Agent, or Firm* — Richard Aron Osman

(57) ABSTRACT

Optical microneedles are adapted for near-infrared or mid-infrared in vivo spectroscopic sensing; and provide a MEMS-based spectrometer for continuous lactate and glucose monitoring by means of a near-infrared or mid-infrared optical microneedle array in a transdermal patch.

29 Claims, 6 Drawing Sheets

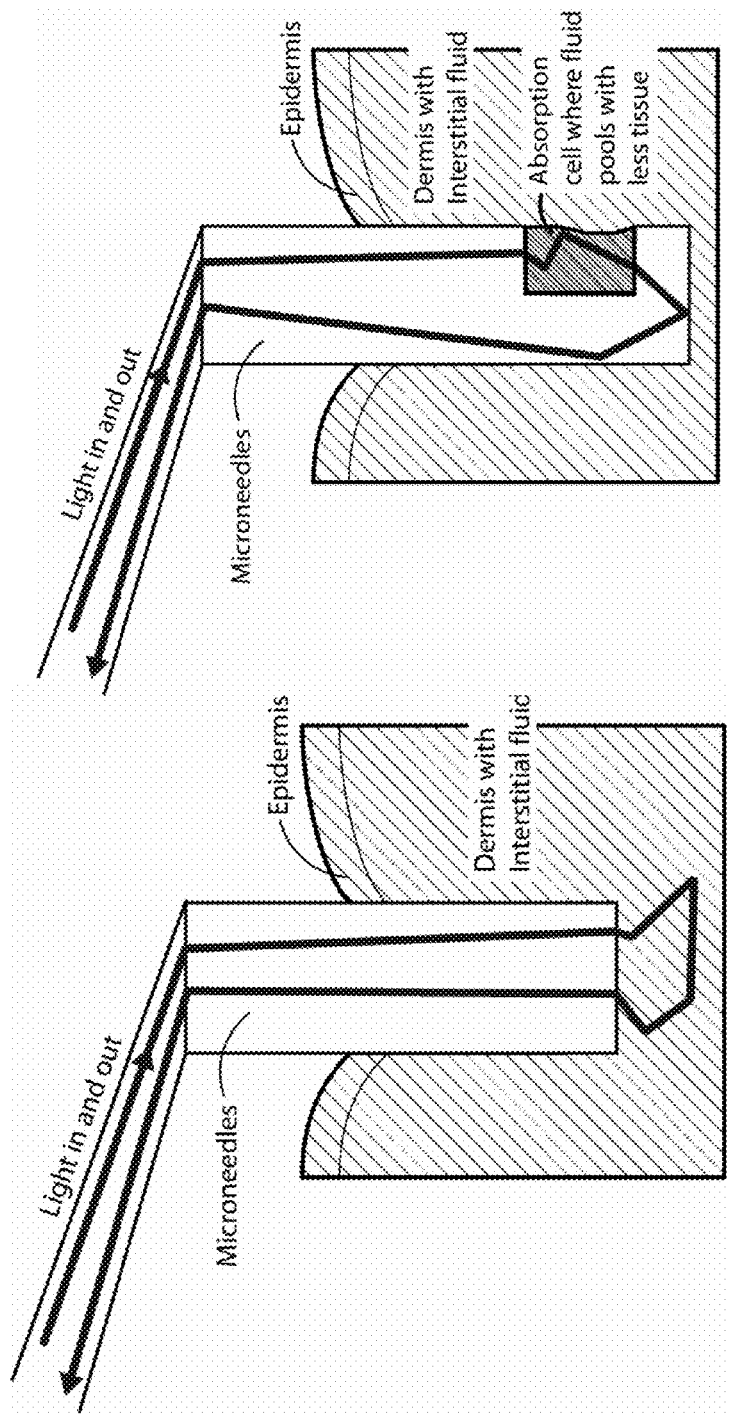

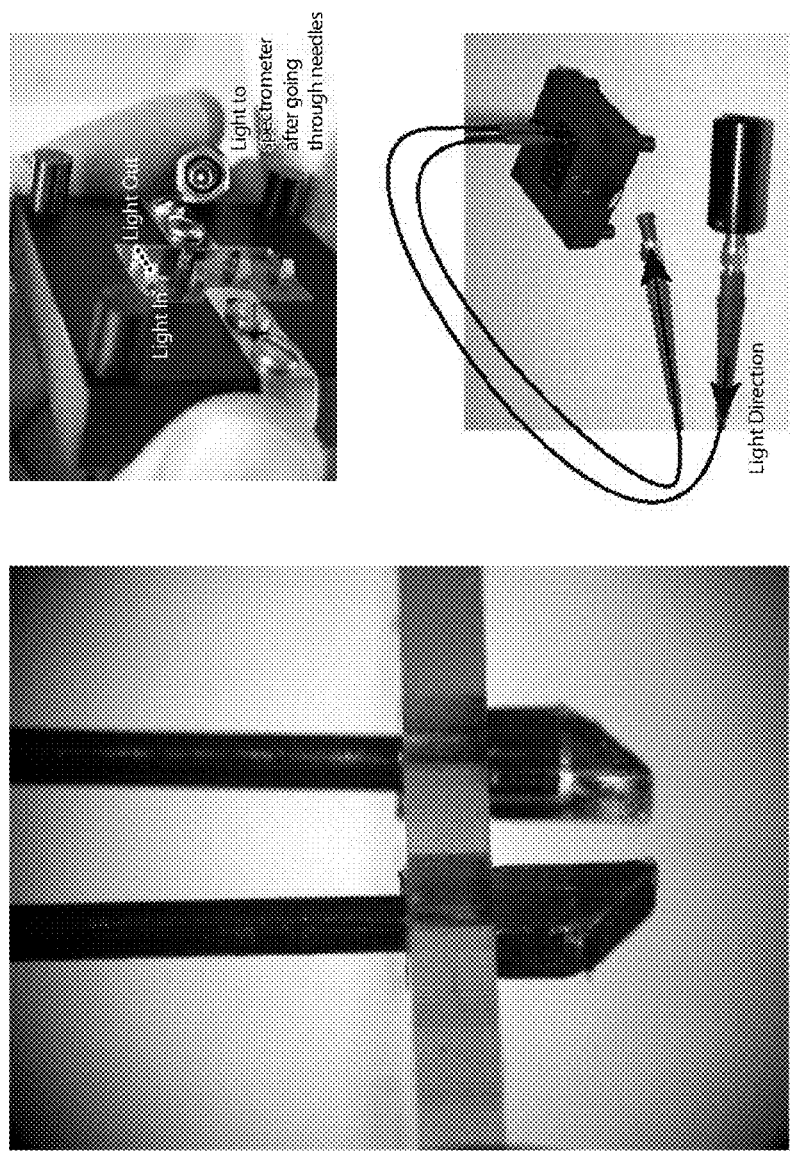
Figure 4 Microneedle demonstration prototype

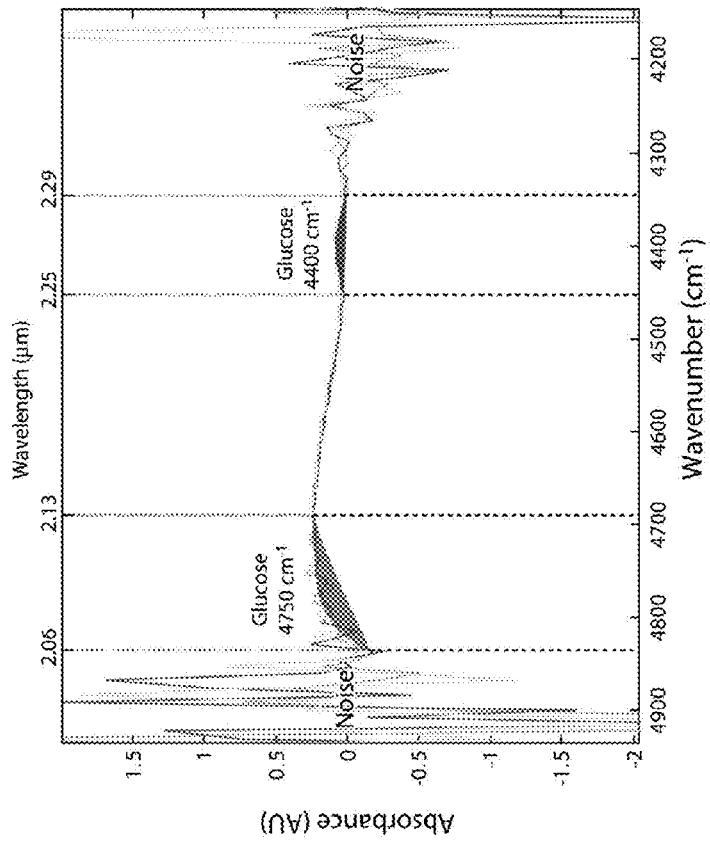
- 480mM glucose measured at 1.5mm needle spacing
  - Two glucose peaks clearly seen
  - Noise Problem
    - 1000X higher than required for selective glucose measurement
    - Intensity at detector 10X too low
    - Probable cause:
      - Optical coupling between fiber optic is poor
Figure 5: Glucose Measurement with Prototype

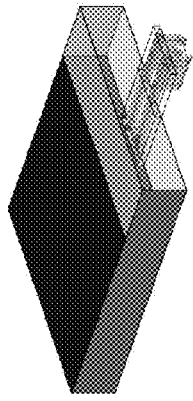

a. Microneedle patch connected to optical interrogator through waveguide structure

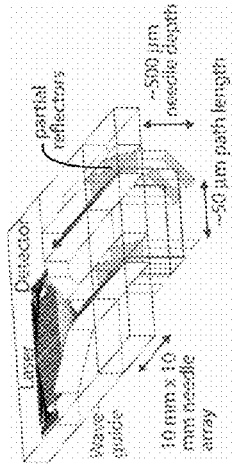

b. Embodiment in which laser consists of several elements, waveguide combines beams and directs light to microneedles

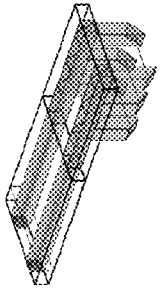

c. Embodiment in which laser consists of an external cavity and single output beam

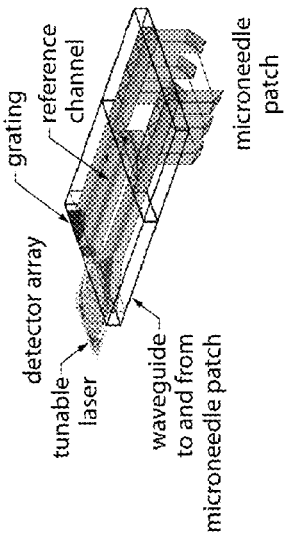

d. Embodiment including a reference channel for input monitoring and grating for wavelength separation at output Figure 6: Optical Interrogator

OPTICAL MICRONEEDLE-BASED SPECTROMETER

This application claims priority to U.S. Ser. No. 61/050,157, filed May 2, 2008.

FIELD OF THE INVENTION

The field of the invention is optical microneedle probe-based spectrometers.

BACKGROUND OF THE INVENTION

There is a need for continuous monitoring of clinical analytes such as lactate, glucose and urea. Sensors for glucose [1] are needed to treat the 300 million worldwide people with diabetes mellitus. But to date, stable, highly accurate and continuous implantable glucose biosensors are not available for the monitoring and treatment of diabetes or any other disease [1]. In vivo measurements of lactate are also important for critical care [2] and metabolic rate determination [3].

A non-invasive device for selective monitoring of physiological fluids and conditions currently does not exist for deployed forces. Unlike civilian use, with popular applications such as glucose monitoring, in-theater, individual combatants require early detection of far more harmful conditions such as dehydration as predicted by lactate levels, or consumption of or exposure to infectious diseases such as malaria. The ability to remotely detect, with a high degree of confidence, the medical status of a serviceperson, stands to dramatically decrease the timeline whereby medical personnel are afforded a more effective way to react.

The disclosed combination of optical microneedles and near-infrared or mid-infrared spectroscopic sensing is original and is a groundbreaking advance for both technologies. Our optical microneedle design is a next step for non-invasive biosampling technology, accommodating MEMS, macroscopic or meso-scale fabrication [4-6]. Recent related developments include miniaturized lactate sensors including thin film electrodes used in catheters and disposable amperometric sensors for on-site analysis [7].

SUMMARY OF THE INVENTION

The invention provides optical microneedles, particularly as adapted for near-infrared or mid-infrared in vivo spectroscopic sensing; and in a particular provides a MEMS-based spectrometer for continuous lactate, glucose, or other analyte monitoring by means of a near-infrared or mid-infrared optical microneedle array in a transdermal patch.

In one embodiment, the invention provides a minimally-invasive device for transdermally analyzing a physiological fluid (for example, blood, saliva, urine, sweat, and in a preferred embodiment, interstitial fluid) comprising (a) an optical microneedle and (b) an optical connector, wherein the optical microneedle comprises a tip adapted to penetrate skin and optically probe physiological fluid, and the optical microneedle and connector are in optical connection such that in operation light from a source is directed through the connector, then through and out the tip of the optical microneedle, then interacts with the physiological fluid which modifies the light by absorption and reflection. Some of the modified signal is reflected back into the microneedle, then through the connector to a detector, such as a spectrometer detector, for optical signal analysis informative of the physiological fluid.

In a particular embodiment, the tip comprises a light-directing notch adapted such that the light is directed to exit and enter the tip at different locations. The notch also serves as a collection area for physiological fluid where there is less tissue to interfere with the optical measurement.

In another embodiment, the invention provides a minimally-invasive device for transdermally analyzing a physiological fluid, comprising (a) an array of optical microneedles and (b) an optical connector, wherein the optical microneedles comprise light-transmitting microneedles and corresponding light-receiving microneedles, and comprise tips adapted and oriented to penetrate skin and optically probe physiological fluid, and the optical microneedles and the connector are in optical connection such that in operation light from a source is directed through the connector, then through and out the tips of the light-transmitting microneedles, then interacts with the physiological fluid before entering the tips of, and being directed through the light-receiving microneedles, and then through the connector to a spectrometer detector for optical signal analysis informative of the physiological fluid. In an alternative embodiment, the spectrometer is on the source side of the tips rather than the receiver side.

In particular embodiments, the tips are sterile; the tips are sterilely packaged; the array comprises preferably between 2 and 10,000, preferably 100 to 10,000 microneedles, optionally ordered and arrayed on and normal to a surface, with the tips distal to the surface; light-reflectors are embossed or coated on the microneedle tips to direct the light into and out of microneedles; the device can be a MEMs-fabricated or machined chip; the device is a skin patch; the light is near or mid infrared, having a wavelength in the range of 700 nm to 20,000 nm; the device is adapted for continuous glucose and lactate monitoring; the device is provided in a monitoring system further comprising the light source and the detector, optionally adapted to multiplex analysis of analytes of the physiological fluid; the microneedles have diameters of 1 to 500 μm, preferably 10 to 100, spacings of 10 to 5000 μm, preferably 100 to 500 and lengths of 10 to 1000 μm, preferably 100 to 500, and combinations of these particular embodiments.

In another embodiment, the invention provides a method of transdermally analyzing a physiological fluid with a subject minimally-invasive device, the method comprising (a) penetrating a skin surface with the microneedle tips; (b) transmitting light from a light source through the light-transmitting microneedles, through physiological fluid beneath the skin surface, through the light-receiving microneedles and to a spectrophotometer detector; and (c) analyzing the light incident at the detector as informative of the physiological fluid.

In another embodiment, the invention provides a method of transdermally analyzing a physiological fluid with a subject minimally-invasive device, the method comprising (a) penetrating a skin surface with the microneedle tips; (b) transmitting light from a light source through a light-transmitting microneedle, through physiological fluid beneath the skin surface, to a nearby microneedle machined and metallized or otherwise coated to provide a retroreflection back to the transmitting microneedle, thereby providing a double pass through the physiological fluid; the light entering the original light transmitting needle and to a spectrophotometer detector; and (c) analyzing the light incident at the detector as informative of the physiological fluid.

In another embodiment, the invention provides a method of transdermally analyzing a physiological fluid with a subject minimally-invasive device, the method comprising (a) penetrating a skin surface with microneedles comprised of an infrared transmitting material with high refractive index; (b) transmitting light from a light source through the infrared transparent, high refractive index microneedles by means of attenuated total reflection, and through physiological fluid beneath the skin surface where an evanescent wave extends into the physiological fluid, interacts with the physiological fluid changing the reflectivity and hence return signal of the light directed back towards the detector and (c) analyzing the light incident at the detector as informative of the physiological fluid.

In a particular embodiment, the subject methods further comprise the step of adjusting the optical path length by selecting multiple, parallel, or series microneedles with or without different lengths to enhance the signal/noise performance of the microneedle for a given target analyte or interferent. In particular, as the absorption of light is proportional to the path length at a given wavelength and for a given target analyte with a characteristic extinction coefficient; therefore optimum performance for a target and rejection of interferents can be aided by the ability to physically or automatically select the path length for a given measurement; hence, multiple path lengths and multiple depths are used to provide a richer data set enhancing the response. In some cases scattering in tissue causes deviation of the absorption from a strict Beers law proportionality with distance. Even in these cases the absorption will increase monotonically with pathlength.

In other embodiments, the subject devices and methods encompass all combinations of the various specific embodiments recited herein, as though they were individually recited.

BRIEF DESCRIPTION OF THE FIGURES

FIG. 2A-2B. depict a single needle embodiment: FIG. 2A is a single needle without notch relying on intrinsic scattering; FIG. 2B is a single needle notched.

FIG. 3A is a microneedle pair; FIG. 3B is a microneedle acting as an attenuated total reflectance device.

FIG. 4 depicts a NIR optical microneedle pair proof-of-principle apparatus, with which we have demonstrated measuring glucose in water.

FIG. 5 depicts measurement of glucose in water using NIR microneedles.

FIG. 6 depicts a MEMS optical interrogator containing a waveguide to direct light from an onboard quantum cascade laser to each needle in a microneedle array patch and back again to an onboard detector.

DETAILED DESCRIPTION OF SPECIFIC EMBODIMENTS OF THE INVENTION

In one embodiment, the invention provides noninvasive optical sensing of glucose, alanine, ascorbate, lactate, triacetin, urea, lipids and drugs, or any combination thereof with an integrated MEMS device using a combination of optical microneedles with innovative infrared optoelectronic devices. The microneedles penetrate the skin and probe physiological fluid, and the optoelectronic devices collect high signal-to-noise ratio (SNR) spectral data. In one embodiment, the MEMS chip provides microneedles normal to the surface and with light reflectors embossed or coated on the tips and in the surface layer such that the light is directed from the source to the needle tips. This light interacts with the physiological fluid before entering the opposing microneedle and then reflects off the bevel down the microneedle and off the reflector to a detector.

Backside light reflectors are optionally molded into a support chip substrate. In one embodiment, we direct light to and from the backside of the chip. The pillars are designed and fabricated with various suitable diameters (such as 1-500 µm, preferably 10-100 µm), spacings (such as 10-5000 µm, preferably 100 to 500 µm), and lengths (such as 10-1000 µm, preferably 100-500 µm). Alternatively, scatter from tissue may be used to reflect light from a source pillar to a receiver pillar.

The pillars are optionally encapsulated with a sacrificial layer to provide pillar support. Bevels are conveniently cut by state-of-the-art end-mill-type machining to ensure bevels on pairs of needles are properly oriented to efficiently get light in and out. The master may be used to fabricate a plastic injection mold and finally fabricate individual plastic chips.

In a particular embodiment of the chip, we use waveguide structures in the chip to bring light to each individual needle from a light source and then bring it from each needle in a microneedle array to a detector.

In a particular embodiment, the invention is a MEMS-based spectrometer for continuous lactate and glucose monitoring by means of an infrared optical microneedle array in a transdermal patch.

Figure 1:
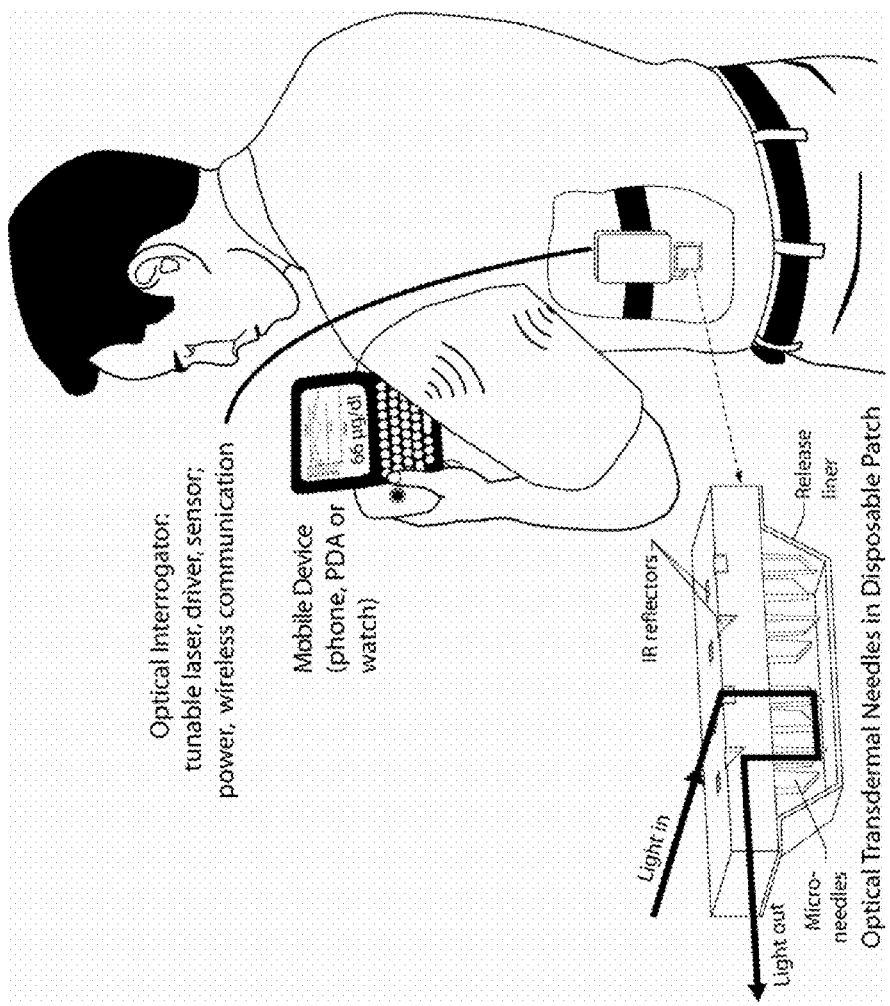
FIG. 1. depicts a non-invasive MEMS embodiment, with optical interrogator (laser, detector, electronics package) and wireless communication display device.

FIG. 1 depicts a non-invasive MEMS embodiment comprising a MEMS-based spectrometer for continuous glucose monitoring using an infrared optical microneedle array in a transdermal patch; a disposable low-cost pain-free or pain-minimal, minimally-invasive microneedle patch with reusable readout and alert, including fiber optic spectrometer or tunable laser and detector, with optional wireless transmitter and wristwatch or cell phone readout and alarm.

FIG. 2 depicts single needle embodiments that enable the needle to act as source and detector conduit. Light is transmitted through the needle where it interacts with the surrounding tissue and physiological fluid. Some of the light reflected from the fluid is then directed through the same needle back to a detector. Several alternative embodiments of the single needle device are disclosed, such as the notched version depicted in FIG. 2B.

For conventional optical absorbance measurements, the light passes directly through the sample being measured. This is the method generally used when two optical microneedle light guides, are inserted into the skin. However, there are other optical measurements compatible with a single optical microneedle; for examples: a) probing absorbance with an evanescent wave, b) probing refractive index through light leakage out of the waveguide either through the sides or bottom retroreflection, or c) probing both absorbance and refractive index through retroreflection.

Absorbance in physiological fluid can be measured in a single light guide microneedle using the attenuated total reflection (ATR) method in which absorption of an evanescent wave is used. [8] For ATR, the light stays inside the needle, but the evanescent wave probes the outside of the needle. This method can be advantageously used in the mid-infrared where absorptions by glucose, lactate, and other analytes are strong [9], allowing measurements with good signal-to-noise ratios even over the small distances probed by the evanescent wave. We have calculated the penetration depth of the evanescent wave into the tissue using the ATR method to be roughly 2-5 microns when MWIR light is used.

To perform evanescent wave measurements in this case, one may use a microneedle light guide or waveguide that has a highly reflective coating at the bottom that retroreflects the light back through the same light guide. A beam splitter or waveplate polarizer combination is used to separate the incoming and retroreflected beams, allowing the retroreflected beam to pass to a spectrometer/detector combination. Fourier transform infrared (FTIR) spectrometers are preferred detectors for the mid-infrared wavelength region when using conventional light sources because of improved signal-to-noise ratios. Absorbance can also be measured using the extension of the light mode field outside the microneedle as described further herein.

One can also use refractive index measurements to monitor glucose or other analytes using a single light guide or microneedle. In this case, the light guide microneedle is configured to be sensitive to the refractive index of the surroundings. This may be done by choosing the light angles in the channel or the needle refractive index such that the amount of light that leaks out of the needle is sensitive to the surrounding refractive index. This is different from the evanescent wave, in which case the light leaking out of the channel does not propagate; the evanescent wave senses the surrounding without light actually leaving the channel. In this case, the loss of light from the needle into the surrounding medium is dependent upon the refractive index of the medium.

Refractive index can also be monitored in retroreflection, in which case the ratio of the refractive index of the channel and the refractive index of the surrounding determines the amount of retroreflection. In either case, retroreflection is used to couple the light back out through a single light guide. The refractive index can be used to determine the amount of an analyte such as glucose in two ways. The refractive index at all wavelengths changes with the concentration of glucose [10], as well as other factors, such as temperature and dehydration.

A preferred method uses the change in refractive index with wavelength to monitor glucose. The glucose mid-infrared absorption produces a corresponding change in the real part of the refractive index as described by the Kramers-Kronig relations. The measured features of the real part of the refractive index tend to be broader than the absorption features. Sharper features can be obtained by differentiating the spectrum. Although there is a change in shape of the features from differentiation, this change of shape is not a limitation when chemometric methods are used to analyze the spectrum, such as partial least squares (PLS), principal component analysis (PCA), or multiple linear regression.

Yet another method for single light guide needle measurements uses the reflectance spectrum taken through the end of the needle. This measurement probes the influence of both absorption (for the light path through the tissue) and refractive index (for the amount of light reflected from the end of the needle, as well as propagation in the tissue. [11]

For the small diameters of the light guide needles necessary to perform relatively painless insertion, the diameter is preferably in the range of 10-90, and preferably 10-50 microns. Since this is not much larger than the wavelength of the light, there will not be very many spatial modes in the light guide. The number of spatial modes is determined by the V-number, which in turn is related to the fiber numerical aperture, core radius, and diameter of the light guide. The numerical aperture is in turn determined by the ratio of the refractive index of the core and cladding of the light guide.

Since there may not be very many modes in the light guide and the light guide diameter is relatively small, the amount of light in a single needle is relatively small. The brightness theorem limits the amount of light that can be coupled from a non-laser source into a small diameter light guide. The amount of light can be increased by using more light guides. However, the pitch of the light guide is limited by the ability to penetrate the tissue. For conventional light sources such as glow bars, the brightness is not very high. Hence, in such embodiments, it is preferably to employ a brighter source such as a laser or superluminescent diode when available.

A tunable light source such as quantum cascade lasers can be used as a source in another embodiment of this device. In this case the wavelength discrimination is done by tuning the source rather than using a spectrometer at the detector. FIG. 6 depicts embodiments of the device using quantum cascade lasers, a planar waveguide, partial reflectors to a needle array, a miniature MWIR detector, and controlling electronics.

Several embodiments of the waveguide are illustrated in FIG. 6. If a laser such as that described by Lee et al.[12] is used, the beams from multiple elements can be combined on the waveguide structure that connects the optical source and detector to the microneedles with a tapered guide as shown in FIG. 6, panel b. If an external cavity laser is used with a single wavelength-tunable output beam, a single waveguide channel such as in FIG. 6, panel c can be used. A waveguide channel for reference signal from the source can be included in the waveguide structure as shown in FIG. 6, panel d. The wavelength of the source can be known to the detector through electronic gating, and or by using a grating at the output with a detector array with each element capturing a separate wavelength bin, as suggested in FIG. 6d. Any or all of these approaches may be combined in a single embodiment.

Rather than using a planar waveguide structure as shown in FIG. 6, panel d, the microneedle patch can also be connected to the source and detector through infrared transmitting fiber optic cables. More or fewer paths than shown in these figures depending on how many microneedles are used and whether or not a different return needle is needed for the detection scheme being implemented.

Figure 3B:
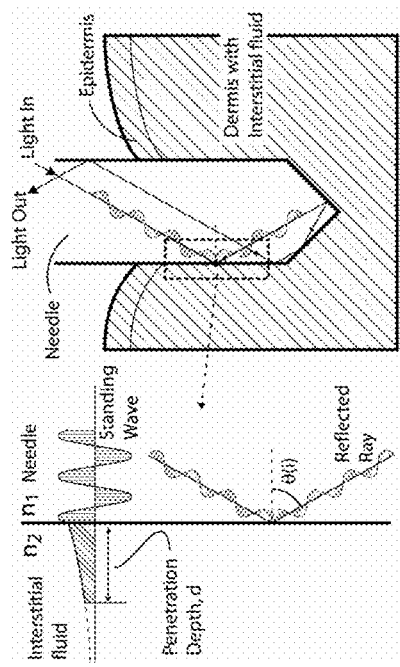
FIG. 3A-3B depict alternative optical microneedle embodiments.
Figure 3A:
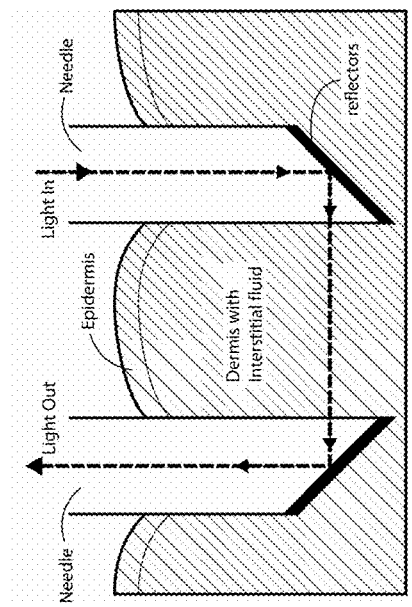

FIG. 3a depicts an optical microneedle used as a single mode waveguide using the light guide as the core and the tissue as the cladding. In this case the mode field diameter is larger than the core (light guide) diameter. Thus the amount of the light field outside the core (light guide) diameter can be used to measure the absorbance of the tissue and its constituents. In general it is desirable to control the amount of light that passes through the sides and end of the light guide. When one does not want light sensitivity to the tissue on the sides of the light guide, a cladding similar to that on an optical fiber can be used. The cladding has a lower refractive index than the core (center) of the light guide to guide the light. When one does want interaction with the tissue on the sides, such as for probing with an evanescent wave, then no cladding should be used. Then, provided that the angles of light in the light guide are sufficiently small and the refractive index ratio between light guide and tissue is sufficiently large, the light will be contained in the light guide and sensitivity is limited to the depth probed by the evanescent wave. Light leakage can be used to sense refractive index change.

FIG. 3b depicts an optical microneedle embodiment that acts as a multimode attenuated total reflectance device. Infrared light is transmitted through the needle where it interacts with surrounding physiological fluid via evanescent waves. Light attenuated by that interaction does not return with the reflected light directed through the same needle back to a detector, reducing the signal allowing the sensor to measure the absorption. Materials for light guides or needles for the mid-IR include, but are not limited to, high-density polyethylene (HDPE), ZnSe, diamond, polycrystalline infrared (PIR) fiber, sapphire, and chalcogenide glasses.

FIG. 4 depicts an optical needle prototype instrument we have used to demonstrate the detection of glucose in an animal model. The optical needles are machined from Poly IR 5 material (Fresnel Technologies, Inc., Fort Worth, Tex.) using standard practices and metallized with aluminum on the bevel to reflect light to a detector. The spectrometer interface on the right contains the microneedles. Light from a near infrared Fourier transform spectrometer (bilithic interferometer with a fiber-optic interface) via the spectrometer interface, which directed the light into the needles, which were inserted into an in vivo animal model. The distance between the needles was adjustable, but for the demonstration experiment was 1.5 mm. The resolution of the spectrometer was 8 cm$^{-1}$, the gain was 4, and 256 interferograms were averaged.

FIG. 5 depicts net analyte glucose signals measured using the near-infrared optical microneedle prototype depicted in FIG. 4.

The subject devices are adapted for multivariate near-infrared sensing using net analyte signal (NAS) theory, a component of the analyte spectrum that is orthogonal to the spectral variance of the background matrix. The NAS is established for successful in vivo tissue measurement, represents selective analyte specific spectral signature, and provides absolute quantitation from in vivo spectra.

We also demonstrated proof-of-concept prototype MEMS analytical systems for noninvasive transdermal monitoring by near-IR spectroscopy, including (1) microneedle light pipes fabricated from biocompatible, optically transparent, mechanically stable materials which were partially metallized to direct the light; (2) a spectrometer interfaced to microneedles and an optical detector; and (3) multivariate processing algorithms to extract the glucose level from signals in tissue/blood.

FIG. 6 depicts a MEMS chip containing waveguides to direct light from a quantum cascade laser to each needle in a microneedle array patch and back again to a detector. The quantum cascade laser may be tunable to give a complete spectrum over a desired spectral band, for example 8 to 10 µm, or fixed wavelengths from separate lasers may be used to interrogated appropriate peak locations to discriminate different analytes using signal processing algorithms embedded in a microprocessor on the sensor.

CITED LITERATURE

[1] Guiseppi-Elie, A., Brahim, S., Slaughter, G. and Ward, K. R., 2005, "Design of a subcutaneous implantable biochip for monitoring of glucose and lactate," *IEEE Sensors Journal*, 5 (3), pp. 345-55.

[2] Lillis, B., Grogan, C., Berney, H. and Lane, B., 2000, "Development of an amperometric biosensor for lactate," presented at 1st Annual International IEEE-EMBS Special Topic Conference on Microtechnologies in Medicine and Biology, Proceedings

[3] Meyerhoff, C., Bischof, F., Mennel, F. J., Sternberg, F., Bican, J. and Pfeiffer, E. F., 1993, "On line continuous monitoring of blood lactate in men by a wearable device based upon an enzymatic amperometric lactate sensor," *Biosensors and Bioelectronics*, 8 (9-10), pp. 409.

[4] Vestel, Michael J., Grummon, David S., Gronsky, Ronald and Pisano, Albert P., 2003, "Effect of Temperature on the Devitrification Kinetics of NiTi Films," *Acta Materialia*, 51 (18), pp. 5309-5318.

[5] Vestel, Michael J. and Grummon, David S., 2004, "Precipitates and Lamellar Microstructures In NiTi Films," *Materials Science and Engineering A*, 378 pp. 437-442.

[6] Vestel, Michael J., 2002, "Effect of Devitrification Temperature on the Microstructure of NiTi Films," Ph.D. thesis, University of California at Berkeley, Berkeley.

[7] Rohm, Ingrid, Genrich, Meike, Collier, Wendy and Bilitewski, Ursula, 1996, "Development of ultraviolet-polymerizable enzyme pastes: bioprocess applications of screen-printed L-lactate sensors," *The Analyst*, 121 (6), pp. 877-881.

[8] J D Kruse-Jarres, G Janatsch, and U Gless, Reagentless determination of glucose and other constituents in blood by ATR-FT-IR-spectroscopy, Clin Chem 1989 35: 1854-1856.

[9] C. Petibois, G. Cazorla, A. Cassaigne, and G. Deleris, "Plasma protein contents determined by Fourier-transform infrared spectrometry, Clinical Chemistry 47; 4, 730-738, (2001)

[10] J. S. Maier, S. A. Walker, S. Fantini, M. A. Franceschini, and E. Gratton, "Possible correlation between blood glucose concentration and the reduced scattering coefficient of tissues in the near infrared," Opt. Lett. 19, 2062-(1994)

[11] Walter M. Doyle, Apparatus and method for normal incidence reflectance spectroscopy, U.S. Pat. No. 5,015, 100 Issued on May 14, 1991

[12] B. G. Lee, M. A. Belkin, R. Audet, J. MacArthur, L. Diehl, C. Pflügl, and F. Capasso, "Widely tunable single-mode quantum cascade laser source for mid-infrared spectroscopy", Applied Physics Letters, 91, 231101, (2007).

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of transdermally analyzing a physiological fluid with a minimally-invasive device for transdermally analyzing a physiological fluid, comprising:

an array of optical microneedles and an optical connector, wherein the optical microneedles comprise mid infrared light-transmitting microneedles and corresponding light-receiving microneedles, and comprise tips adapted and oriented to penetrate skin and optically probe physiological fluid, and the optical microneedles and the connector are in an optical path configured to pass mid infrared light from a source through the connector, then through and out the tips of the light-transmitting microneedles, to then interact with the physiological fluid before entering the tips of, and passing through the light-receiving microneedles, and then through the connector to a spectrometer detector for optical signal analysis informative of the physiological fluid, the method comprising:

penetrating a skin surface with the microneedle tips;

transmitting light from a light source through the light-transmitting microneedles, through physiological fluid beneath the skin surface, through the light-receiving microneedles and to a detector which can discriminate the wavelength dependent transmission, either by using a wavelength discriminating source or spectrometer at the output end of the instrument; and analyzing the light incident at the detector as informative of the physiological fluid, and further comprising the step of adjusting the optical path length by selecting multiple, parallel, or series microneedles with or without different lengths to enhance the signal/noise performance of the microneedles for a given target analyte or interferent.

2. The method of claim 1, which provides multiple wavelength measurements using a spectrometer on either the source or detector side, and comprises a tunable light source or a multiwavelength light source array.

3. The method of claim 1 wherein the tips are sterile.

4. The method of claim 1 wherein the tips are sterilely packaged.

5. The method of claim 1 wherein the array comprises between 2 and 10,000 microneedles.

6. The method of claim 1 wherein the array comprises between 2 and 10,000 microneedles arrayed on and normal to a surface, with the tips distal to the surface.

7. The method of claim 1 wherein the array is a pair of microneedles.

8. The method of claim 1 wherein light-reflectors are embossed or coated on the microneedle tips to direct the light into and out of microneedles.

9. The method of claim 1, wherein the microneedles comprise a material selected from the group consisting of high-density polyethylene (HDPE), ZnSe, diamond, polycrystalline infrared (PIR) fiber, sapphire, and chalcogenide glasses.

10. The method of claim 1, wherein the microneedles comprise a material that is diamond.

11. The method of claim 1, wherein the device is a MEMs-fabricated chip.

12. The method of claim 1, wherein the device further comprises disposable planar and/or MEMS waveguides structures to couple and direct the light to and from the microneedles, source and detector.

13. The method of claim 1, wherein the device is a skin patch.

14. The method of claim 1, wherein the microneedles comprise a material selected from the group consisting of high-density polyethylene (HDPE), ZnSe, diamond, polycrystalline infrared (PIR) fiber, sapphire, and chalcogenide glasses.

15. The method of claim 1, wherein the microneedles comprise a material that is diamond.

16. The method of claim 1, wherein the device is adapted for continuous glucose, alanine, ascorbate, lactate, triacetin, urea or drug monitoring.

17. The method of claim 1 wherein the device is part of a monitoring system comprising the device, the light source and the detector.

18. The method of claim 17 wherein the source is wavelength tunable.

19. The method of claim 17 wherein the source is a tunable laser device rather than a broadband source which then must be scanned at the detector stage.

20. The method of claim 17 wherein the source comprises a quantum cascade laser.

21. The method of claim 17 further comprising quantum cascade lasers, a planar waveguide, partial reflectors to the array of optical microneedles, a miniature MWIR detector, and controlling electronics.

22. The method of claim 17 wherein the light source is broadband or tunable and the detector is wavelength discriminating.

23. The method of claim 17 wherein the system is adapted to multiplex analysis of analytes of the physiological fluid.

24. The method of claim 1, wherein the microneedles have diameters of 1 to 500 µm, spacings of 10 to 5000 µm, and lengths of 10 to 1000 µm.

25. The method of claim 1 wherein the microneedles act as miniature attenuated total reflection waveguides or crystals, creating evanescent waves which interact with the physiological fluid, and the light absorbed by the evanescent waves is discriminated by the detector, which can characterize the absorption as a function of wavelength.

26. The method of claim 1 wherein the microneedles act as a single-mode waveguide wherein either an attached cladding contains the mode or the tissue acts as a cladding to contain the mode.

27. The method of claim 1 wherein retroreflection from the microneedle tips serves to monitor both absorption and/or refractive index in the tissue.

28. The method of claim 1 wherein the microneedles probe absorption in the physiological fluid through the Kramers Kronig relationship using measurements of refractive index with or without absorption measurements.

29. The method of claim 1 wherein the microneedles probe the analyte concentration through changes in refractive index.

* * * * *